US009839676B2

(12) United States Patent
Hobman et al.

(10) Patent No.: US 9,839,676 B2
(45) Date of Patent: Dec. 12, 2017

(54) METHODS OF TREATING CANCER USING ANGIOGENIN OR AN ANGIOGENIN AGONIST (71) Applicants: Murray Goulburn Co-Operative Co., Limited, Southbank, Victoria (AU); AGRICULTURE VICTORIA SERVICES PTY LTD, Attwood, Victoria (AU)

(72) Inventors: Peter Hobman, Melbourne (AU); Andrew Brown, Cobram (AU)

(73) Assignees: Murray Goulburn Co-Operative Co., Limited, Southbank (AU); AGRICULTURE VICTORIA SERVICES PTY LTD, Attwood (AU)

( * ) Notice: Subject to any disclaimer, the term of this patent is extended or adjusted under 35 U.S.C. 154(b) by 0 days.

(21) Appl. No.: 14/399,852

(22) PCT Filed: May 10, 2013

(86) PCT No.: PCT/AU2013/000478
§ 371 (c)(1),
(2) Date: Nov. 7, 2014

(87) PCT Pub. No.: WO2013/166555
PCT Pub. Date: Nov. 14, 2013

(65) Prior Publication Data
US 2015/0104438 A1    Apr. 16, 2015

(30) Foreign Application Priority Data

May 10, 2012  (AU) ............................... 2012901918
Apr. 12, 2013  (AU) ............................... 2013204740

(51) Int. Cl.
*A61K 38/46*   (2006.01)
*C07K 14/515*  (2006.01)
*A61K 45/06*   (2006.01)
*A61K 38/18*   (2006.01)
*C12N 9/22*    (2006.01)

(52) U.S. Cl.
CPC ........ *A61K 38/465* (2013.01); *A61K 38/1891* (2013.01); *A61K 45/06* (2013.01); *C07K 14/515* (2013.01); *C12N 9/22* (2013.01); *C12Y 301/27* (2013.01)

(58) Field of Classification Search
None
See application file for complete search history.

(56) References Cited

U.S. PATENT DOCUMENTS

| | | |
|---|---|---|
| 5,171,845 A | 12/1992 | Spik et al. |
| 5,596,082 A | 1/1997 | Kussendrager et al. |
| 6,010,698 A | 1/2000 | Kussendrager et al. |
| 8,067,360 B2 | 11/2011 | Knopf et al. |
| 8,114,969 B2 | 2/2012 | Vincent et al. |
| 8,298,801 B2 * | 10/2012 | Kink ........................ C12N 9/22 424/94.6 |
| 8,440,183 B2 | 5/2013 | Naidu et al. |
| 8,551,547 B2 | 10/2013 | Brown et al. |
| 9,119,818 B2 | 9/2015 | McDonagh et al. |
| 2005/0037955 A1 | 2/2005 | Hooper et al. |
| 2007/0253941 A1 | 11/2007 | Naidu et al. |
| 2007/0275036 A1 | 11/2007 | Green, III et al. |
| 2008/0045546 A1 | 2/2008 | Bouchon et al. |
| 2009/0099128 A1 | 4/2009 | Wu |
| 2009/0305972 A1 | 12/2009 | Chahal et al. |
| 2011/0123514 A1 | 5/2011 | McDonagh et al. |
| 2011/0151016 A1 | 6/2011 | McDonagh et al. |
| 2011/0262422 A1 | 10/2011 | Cocks et al. |
| 2014/0370087 A1 | 12/2014 | Kim et al. |

FOREIGN PATENT DOCUMENTS

| | | |
|---|---|---|
| AU | 2008902371 A1 | 5/2008 |
| AU | 2009246053 B2 | 7/2014 |
| EP | 0704218 A2 | 4/1996 |
| EP | 0786473 A2 | 7/1997 |
| EP | 0869134 A1 | 10/1998 |
| JP | H08511236 A | 11/1996 |
| JP | H10-7585 A | 1/1998 |
| JP | 2001-521733 A | 11/2001 |
| JP | 2003-144095 A | 5/2003 |
| JP | 2004-331566 A | 11/2004 |
| JP | 2005-507637 A | 3/2005 |

(Continued)

OTHER PUBLICATIONS

Maes et al, "The complete amino acid sequence of bovine milk angiogenin," FEBS Lett. 241(1-2):41-5 (1988).
Tsuda et al., "Cancer prevention by bovine lactoferrin and underlying mechanisms—a review of experimental and clinical studies," Biochem Cell Biol. 80(1):131-6 (2002).
First Examination Report for New Zealand Application No. 631749, dated Mar. 5, 2015 (3 pages).
Second Examination Report for Australian Patent Application No. 2013204721, dated Jul. 10, 2015 (11 pages).
International Preliminary Report on Patentability for International Application No. PCT/AU/2013/000478, dated Apr. 2, 2014 (8 pages).
International Search Report for International Application No. PCT/AU2013/000478, dated Jun. 13, 2013 (3 pages).
Extended European Search Report for International Application No. PCT/AU2013000478, dated Oct. 30, 2015 (7 pages).
International Search Report for International Application No. PCT/AU2013/000480, dated Jun. 26, 2013 (2 pages).

(Continued)

*Primary Examiner* — Allison Fox
(74) *Attorney, Agent, or Firm* — Clark & Elbing LLP (57) ABSTRACT

The invention provides a method for treating cancer in a subject or a method of inducing an anti-tumour effect including reducing tumour volume, inhibiting or slowing tumour growth, inhibiting tumour progression, altering the metabolic activity of a tumour, inducing quiescence of a tumour, inhibiting or reducing metastasis, inhibiting or reducing tumour invasiveness, reducing tumour weight, reducing tumour neovascularisation, improving time to disease progression (TDP) and/or improving survival, the method comprising administering to the subject an effective amount of angiogenin or an angiogenin agonist.

7 Claims, 2 Drawing Sheets (56) References Cited

FOREIGN PATENT DOCUMENTS

| | | |
|---|---|---|
| JP | 2007-526337 A | 9/2007 |
| JP | 2009-543868 A | 12/2009 |
| JP | 2011-519962 A | 7/2011 |
| KR | 2005-0091015 A | 9/2005 |
| RU | 2110066 C1 | 4/1998 |
| RU | 2204262 C2 | 5/2003 |
| RU | 2008145662 A | 6/2010 |
| WO | WO-94/21288 A1 | 9/1994 |
| WO | WO-99/23112 A1 | 5/1999 |
| WO | WO-99/58126 A1 | 11/1999 |
| WO | WO-01/00792 A1 | 1/2001 |
| WO | WO-02/052022 | 7/2002 |
| WO | WO-02/068650 A2 | 9/2002 |
| WO | WO-2004/058988 A2 | 7/2004 |
| WO | WO-2004/106491 A2 | 12/2004 |
| WO | WO-2005/072764 A2 | 8/2005 |
| WO | WO-2005/084699 A1 | 9/2005 |
| WO | WO-2006/002106 A2 | 1/2006 |
| WO | WO-2006/054277 A2 | 5/2006 |
| WO | WO-2007/013666 A2 | 2/2007 |
| WO | WO-2007/023479 A2 | 3/2007 |
| WO | WO-2007/075396 A2 | 7/2007 |
| WO | WO-2007/127183 A1 | 11/2007 |
| WO | WO-2008/010991 A2 | 1/2008 |
| WO | WO-2009/043455 A2 | 4/2009 |
| WO | WO-2009/137879 A1 | 11/2009 |
| WO | WO-2009/137880 A1 | 11/2009 |
| WO | WO-2009/137881 A1 | 11/2009 |
| WO | WO-2011/060488 A1 | 5/2011 |
| WO | WO-2011/060489 A1 | 5/2011 |
| WO | WO-2011063160 A1 | 5/2011 |
| WO | WO-2013/166555 A1 | 11/2013 |
| WO | WO-2013/166557 A1 | 11/2013 |

OTHER PUBLICATIONS

Olson et al., "A monoclonal antibody to human angiogenin suppresses tumor growth in athymic mice," Cancer Res. 54(17):4576-9 (1994).

Piccoli et al., "Chimeric anti-angiogenin antibody cAb 26-2F inhibits the formation of human breast cancer xenografts in athymic mice," Proc Natl Acad Sci USA. 95(8):4579-83 (1998).

Further Examination Report for New Zealand Application No. 708616, dated Aug. 27, 2015 (2 pages).

"Comparing Distributions: Z Test," <http://homework.uoregon.edu/pub/class/es202/ztest.html>, retrieved Jun. 8, 2016 (4 pages).

National Cancer Institute, "Angiogenesis Inhibitors," <http://www.cancer.gov/about-cancer/treatment/types/immunotherapy/angiogenesis-inhibitors-fact-sheet>, retrieved Jun. 10, 2016 (3 pages).

English Translation of Notice of Reason for Rejection for Japanese Application No. 2015-517471, dated Feb. 7, 2017 (3 pages).

Acharya et al., "Crystal structure of human angiogenin reveals the structural basis for its functional divergence from ribonuclease," Proc Natl Acad Sci USA. 91(8): 2915-19 (1994).

Fedorova et al., "Milk ultrafiltrate as a promising source of angiogenin," Appl Biochem and Microbio. 38(2):193-6 (2002).

First Examination Report for Indian Application No. 8876/DELNP/2010, dated Apr. 28, 2017 (9 pages).

Gao et al., "Identification and characterization of follistatin as a novel angiogenin-binding protein," FEBS Lett. 581(28):5505-10 (2007).

Gao et al., "Mechanisms of action of angiogenin," Acta Biochim Biophys. Sin. 40(7):619-624 (2008).

Jang et al., "High level production of bovine angiogenin in $E.\ coli$ by an efficient refolding procedure," Biotechnol Lett. 26(19):1501-4 (2004).

Kieran et al., "Control of motoneuron survival by angiogenin," J Neurosci. 28(52):14056-61 (2008).

Ng et al., "Inhibition of human immunodeficiency virus type 1 reverse transcriptase, protease and integrase by bovine milk proteins," Life Sci. 69(19):2217-23 (2001).

Office Action for European Application No. 13787726.2, dated Apr. 24, 2017 (6 pages).

Official Action for Russian Application No. 2014149807, dated May 10, 2017 (12 pages).

Rustam'yan et al., "Penetration of cow milk angiogenin into the blood of mice after peroral introduction," Biol Bull. 29(2):165-7 (2002).

Subramanian et al., "Human angiogenin is a neuroprotective factor and amyotrophic lateral sclerosis associated angiogenin variants affect neurite extension/pathfinding and survival of motor neurons," Hum Mol Genet. 17(1):130-49 (2008).

van den Berg et al., "Patterns of expression of the Follistatin and Follistatin-like1 genes during chicken heart development: a potential role in valvulogenesis and late heart muscle cell formation," Anat Rec (Hoboken) 290(7):783-7 (2007).

Xu et al., "Angiogenin activates human umbilical artery smooth muscle cells," Biochem Biophys Res Commun. 285(4) 909-14 (2001).

* cited by examiner

| Group | | (..........................Tissue collection..................................................) | | | | |
|---|---|---|---|---|---|---|
| | | Day 0 | Day 12 | | Day 21 | Day 29 |
| Control | Induce Cancer | 10 | 10 | Cancer-Cachexia Present | 10 | 10 |
| Induction | Induce Cancer | | 10 | Cancer-Cachexia Present | 10 | 10 |
| Tumour | Induce Cancer | | 10 | Cancer-Cachexia Present | 10 | 10 |
| | | (...................................Treatment Period...................................................) | | | | |

Figure 3

METHODS OF TREATING CANCER USING ANGIOGENIN OR AN ANGIOGENIN AGONIST

FIELD

The present invention relates to methods for treating cancer, including inhibiting tumour growth, reducing tumour volume, inhibiting tumour progression, inhibiting metastasis and improving survival.

BACKGROUND

Cancers are characterised by abnormal and uncontrolled cellular proliferation. Cancer can affect any tissue in the body and can spread outside the tissue of origin. Uncontrolled cell growth, cell death and other cellular abnormalities can lead to the formation of cancerous tumours. Tumours can disrupt the function of and destroy the tissues in which they originate and when cancer cells metastasize, secondary tumours can develop adjacent to, or remote from, the site of primary growth.

Available anti-cancer therapies include chemotherapeutic agents, immunotherapeutic agents, exposure to radiation and surgery. There is a need in the art for additional therapeutic approaches for the treatment of cancer and for the prevention of cancer progression and tumour growth.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art.

SUMMARY

A first aspect provides a method for treating cancer in a subject, the method comprising administering to the subject an effective amount of angiogenin or an angiogenin agonist.

In an alternative form the first aspect provides angiogenin or an angiogenin agonist for treating cancer in a subject or use of angiogenin or an angiogenin agonist in the manufacture of a medicament for treating cancer.

A second aspect provides a method of inducing an anti-tumour effect comprising administering an effective amount of angiogenin or an angiogenin agonist.

In an alternative form the second aspect provides angiogenin or an angiogenin agonist for inducing an anti-tumour effect in a subject or use of angiogenin or an angiogenin agonist in the manufacture of a medicament for inducing an anti-tumour effect.

In an embodiment of the second aspect the anti-tumour effect is selected from reducing tumour volume, inhibiting tumour growth, inhibiting tumour progression, altering the metabolic activity of a tumour, inducing quiescence of a tumour, inhibiting or reducing metastasis, inhibiting or reducing tumour invasiveness, reducing tumour weight, reducing tumour neovascularisation, improving time to disease progression (TDP) and improving survival.

In an embodiment of the first and second aspects the angiogenin agonist is a milk extract enriched for angiogenin, optionally by cation exchange.

The inventors have found that angiogenin and a bovine milk extract enriched for angiogenin increased quadricep muscle weight and reduced abdominal fat pad weight when fed a diet including bovine angiogenin. The demonstrated role of angiogenin in increasing lean muscle mass and decreasing fat mass indicates that methods involving administering angiogenin or an angiogenin agonist have a broad variety of applications where an increase in muscle tissue would be therapeutically beneficial, such as in livestock production, muscle disorders and for general fitness and physique.

As angiogenin is implicated in cancer, the inventors tested their milk extract in a mouse cancer model to evaluate its safety profile. Surprising the extract was shown to delay tumour onset and reduce tumour volume in the mouse model. This was particularly unexpected and contrary to the teaching of the prior art. Accordingly the inventors propose that a milk extract enriched for angiogenin and therefore angiogenin, are useful to prevent or slow tumour growth and treat tumour size, thereby preventing or treating cancer.

In some embodiments the methods of the first and second aspects further comprise administering to the subject one or more chemotherapeutic agents, radiotherapy or both.

The chemotherapeutic agent may be administered simultaneously, separately or sequentially with angiogenin or the angiogenin agonist and if sequential or separate may be administered in any order.

The methods of the first and second aspect may further comprise administering a chemoprotective agent. Such agents may be used with certain chemotherapy programs to reduce or minimize the effects of chemotherapy on the body.

In one embodiment of the first or second aspects angiogenin or angiogenin agonist is administered orally.

A third aspect provides a composition comprising angiogenin or an angiogenin agonist and a chemotherapeutic agent.

In an embodiment of any of the first to third aspects the angiogenin is recombinant angiogenin, preferably human or bovine recombinant angiogenin.

In an embodiment of any of the first to third aspects the angiogenin is provided as an enriched extract from milk or plasma, particularly from bovine milk or from bovine or human plasma. Such an enriched extract is an angiogenin agonist, in that it is not pure angiogenin but provides angiogenin.

DETAILED DESCRIPTION

Angiogenin is a 14 kDa, non-glycosylated polypeptide which is produced by several growing cell types including vascular endothelial cells, aortic smooth muscle cells, fibroblasts, and some tumours such as colon carcinomas, ovarian carcinomas, and breast cancers. Angiogenin has been isolated from a number of sources including normal human plasma, bovine plasma, bovine milk, and mouse, rabbit and pig sera.

Angiogenin is homologous to pancreatic ribonuclease and has distinct ribonucleolytic activity. The protein is able to induce new blood vessel growth; however, it has not been established what role the ribonucleolytic activity of angiogenin plays in angiogenesis induced by this protein.

As well as a potent stimulator of angiogenesis, angiogenin has been shown to possess a number of other activities. However there is no previous disclosure of angiogenin's effect on cancer cells.

The invention in one aspect relates to the treatment of cancer.

"Treating" or "treatment" refers to both therapeutic treatment and prophylactic or preventative measures, wherein the aim is to prevent, ameliorate, reduce or slow down (lessen) cancer. Treatment as used herein includes reducing tumour volume, inhibiting tumour growth, inhibiting tumour progression, altering the metabolic activity of a tumour, inducing quiescence of a tumour, inhibiting or reducing metastasis, inhibiting or reducing tumour invasiveness, reducing tumour weight, reducing tumour neovascularisation, improving time to disease progression (TDP) and improving survival.

Treating also includes making the cancer or cancer cell susceptible (or more susceptible) to treatment with another anti-cancer therapy.

"Preventing", "prevention", "preventative" or "prophylactic" refers to keeping the cancer from occurring, or to hinder, defend from, or protect from the occurrence of a cancer, including an abnormality or symptom. A subject in need of prevention may be prone to develop cancer or may possess one or more cancer markers.

The term "ameliorate" or "amelioration" refers to a decrease, reduction or elimination of cancer, including an abnormality or symptom. A subject in need of treatment may already have cancer or may be prone to have cancer, may possess one or more cancer markers, may have been diagnosed with a tumour, may be free from tumours and the cancer may be metastatic or pre-metastatic.

The "subject" includes a mammal. The mammal may be a human, or may be a domestic, zoo, companion or environmentally valuable animal. While it is particularly contemplated that the methods of the invention are suitable for medical treatment of humans, they are also applicable to veterinary treatment, including treatment of companion animals such as dogs and cats, and domestic animals such as horses (including race horses), cattle and sheep, or zoo animals such as felids, canids, bovids, and ungulates or environmentally valuable animals such as the Tasmanian devil. A subject may be afflicted with cancer or may not be afflicted with cancer (i.e., free of detectable disease). A subject may have or be susceptible to developing a malignancy, a cancer, a tumour or any neoplastic disease or disorder.

The terms "cancer" and "cancerous" refer to or describe the physiological condition in mammals that is typically characterized by unregulated cell growth. The methods of the present invention may be used to treat a cancer associated with the formation of solid tumours, including carcinomas, or a haematological malignancy.

Cancers associated with the formation of solid tumours that may be treated by the methods of the invention include carcinomas such as adenocarcinomas and epithelial carcinomas, squamous cell cancer, lung cancer, small-cell lung cancer, non-small cell lung cancer and large cell carcinoma types, colon cancer, colon metastasized to liver cancer, colorectal cancer, breast cancer, ovarian cancer, kidney cancer, renal cancer, cancer of the bladder, liver cancer, hepatocellular carcinoma, cancer of the gastrointestinal tract, rectal cancer, esophageal cancer, pancreatic cancer, stomach cancer, gynecological cancers including cervical, vulval, uterine and endometrial cancers, prostate cancer, testicular cancer, nasopharyngeal cancer, thyroid cancer, thyroid papillary carcinoma, cancer of the head, neck or brain, nervous system cancers, including neuroblastomas, skin cancers including melanomas, sarcomas, including osteosarcomas and Ewing's sarcoma, glioblastoma and salivary gland carcinoma.

A haematological malignancy is a cancer that affects blood, bone marrow and lymph nodes and includes leukaemia, lymphomas and myeloma. Such malignancies are typically associated with the formation of non-solid tumours or non-solid tumour masses.

Haematological malignancies that may be treated by the methods of the present invention include leukaemia including acute lymphoblastic leukaemia, chronic lymphocyte leukaemia, acute myelogenous leukaemia, chronic myelogenous leukaemia, hairy cell leukaemia, leukemic reticuloendotheliosis, myelogenous leukaemia, lymphoma including Hodgkin's lymphoma and non-Hodgkin lymphoma, mature B cell neoplasms, mature T and natural killer cell neoplasms, immunodeficiency-associated lymphoproliferative disorders, histiocytic and dendritic cell neoplasms and myelomas such as multiple myelomas.

The cancer may be advanced, at stage I, II, III or IV.

Since angiogenin is highly conserved in sequence and function across species, the methods of the invention are applicable in non-human mammals or avian species [e.g. domestic animals (e.g., canine and feline), sports animals (e.g., equine), food-source animals (e.g., bovine, porcine and ovine), avian species (e.g., chicken, turkey, other game birds or poultry)] wherein the presence of myostatin causes or contributes to undesirable pathological effects or decrease of myostatin levels has a therapeutic benefit.

The angiogenin or angiogenin agonist may be provided as a pharmaceutical, veterinary or neutraceutical composition or as a food.

A pharmaceutical composition is one which is suitable for administration to humans. A veterinary composition is one that is suitable for administration to animals. Generally such compositions will contain purified angiogenin or angiogenin agonist or at the very least all components of the composition will be verifiable.

The compositions used in the methods of the first and second aspects may comprise one or more carriers and optionally other therapeutic agents. Each carrier, diluent, adjuvant and/or excipient may be pharmaceutically "acceptable".

By "pharmaceutically acceptable carrier" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmaceutically acceptable" salt or ester of a novel compound as provided herein is a salt or ester which is not biologically or otherwise undesirable.

As used herein, a "pharmaceutical carrier" is a pharmaceutically acceptable solvent, suspending agent or vehicle for delivering the agent to the subject. The carrier may be liquid or solid and is selected with the planned manner of administration in mind. Each carrier must be pharmaceutically "acceptable" in the sense of being not biologically or otherwise undesirable i.e. the carrier may be administered to a subject along with the agent without causing any or a substantial adverse reaction.

The composition may be administered orally, topically, or parenterally in formulations containing conventional non-toxic pharmaceutically acceptable carriers, adjuvants, and vehicles.

The term parenteral as used herein includes intravenous, intraarterial, intraperitoneal, intramuscular, subcutaneous, subconjunctival, intracavity, transdermal and subcutaneous injection, aerosol for administration to lungs or nasal cavity or administration by infusion by, for example, osmotic pump.

The composition may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. Tablets may contain the agent in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. The agent may be encapsulated, micro-encapsulated or contained in nanoparticles.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

The compositions may also contain other active compounds providing supplemental, additional, or enhanced therapeutic functions. The pharmaceutical compositions may also be included in a container, pack, or dispenser together with instructions for administration.

Chemotherapeutic agents suitable for use with the methods of the first and second aspects and the composition of the third aspect include, for example, alkylating agents, nitrosoureas, antimetabolites, anthracyclines and related drugs, anti-tumour antibiotics, topoisomerase I or II inhibitors, corticosteroid hormones and microtubule poisons.

Alkylating agents include:
Mustard gas derivatives: Mechlorethamine, Cyclophosphamide, Chlorambucil, Melphalan, and Ifosfamide,
Ethylenimines: Thiotepa and Hexamethylmelamine,
Alkylsulfonates: Busulfan,
Hydrazines and triazines: Altretamine, Procarbazine, Dacarbazine and
Temozolomide,
Nitrosureas: Carmustine, Lomustine and Streptozocin,
metal salts: Carboplatin, Cisplatin, and Oxaliplatin.
Plant alkaloids include:
Vinca alkaloids: Vincristine, Vinblastine and Vinorelbine,
Taxanes: Paclitaxel and Docetaxel,
Podophyllotoxins: Etoposide and Tenisopide,
Camptothecan analogs: Irinotecan and Topotecan.
Anti-tumour antibiotics include:
Anthracyclines: Doxorubicin, Daunorubicin, Epirubicin, Mitoxantrone, and Idarubicin,
Chromomycins: Dactinomycin and Plicamycin,
Miscellaneous: Mitomycin and Bleomycin.
Anti-metabolites include:
Folic acid antagonist: Methotrexate,
Pyrimidine antagonist: 5-Fluorouracil, Foxuridine, Cytarabine, Capecitabine, and Gemcitabine,
Purine antagonist: 6-Mercaptopurine and 6-Thioguanine,
Adenosine deaminase inhibitor: Cladribine, Fludarabine, Nelarabine and Pentostatin.
Topoisomerase inhibitors include:
Topoisomerase I inhibitors: Ironotecan, topotecan,
Topoisomerase II inhibitors: Amsacrine, etoposide, etoposide phosphate and teniposide.
Miscellaneous anti-neoplastics include:
Ribonucleotide reductase inhibitor: Hydroxyurea, Adrenocortical steroid inhibitor:
Mitotane,
Enzymes: Asparaginase and Pegaspargase,
Antimicrotubule agent: Estramustine,
Retinoids: Bexarotene, Isotretinoin, Tretinoin (ATRA).

Beyond the chemotherapeutic agents listed above, many other types of chemotherapies exist, such as targeted cancer therapy, immunotherapy, and hormone therapy and agents for use in such therapies fall within the definition of "chemotherapeutic agent" as used herein.

Targeted cancer therapies include:
Signal Transduction inhibitors: Imatinib Mesylate (protein-tyrosine kinase inhibitor), Genefitinib (epidermal growth factor receptor tyrosine kinase inhibitor—EGFR-TK), Cetuximab (epidermal growth factor receptor), Lapatinib (epidermal growth factor receptor (EGFR) and human epidermal receptor type 2 (HER2) tyrosine kinase inhibitor,
Biologic Response Modifier Agent: Denileukin Diftitox,
Proteasome inhibitor: Bortezomib, Monoclonal antibodies: Alemtuzumab, Gemtuzumab ozogamicin, Rituximab, Trastuzumab, Ibritumomab, Bevacizumab, Erlotinib, Gefitinib and Tioxetan.
Immunotherapies include:
Cytokines: interleukins and interferon,
Colony Stimulating factors,
Tumour vaccines.

Hormone therapies include:
Adrenal steroid inhibitors: aminoglutethimide, mitotane
Androgens: fluoxymesterone, testosterone, testolactone,
Anti-androgens: bicalutamide, flutamide, nilutamide,
Antiestrogens: tamoxifen, toremifene,
Aromatase inhibitors: anastrazole, exemestane, letrozole,
Estrogens: DES(diethylstilbestrol), estradiol(estrace), premarin,
LHRH agonists: goserelin acetate, leuprolide acetate, triptorelin pamoate,
Progestational agent: medroxyprogesterone acetate, hydroxyprogesterone caproate, megestrol, progestins,
Selective Estrogen Receptor Modulators (SERMs): Raloxifene.

The angiogenin or composition comprising angiogenin can be administered in one dose, or at intervals such as once daily, once weekly, and once monthly.

Dosage schedules can be adjusted depending on the half life of angiogenin or its agonist, or the severity of the patient's condition.

Generally, the compositions are administered as a bolus dose, to maximize the circulating levels of angiogenin for the greatest length of time after the dose. Continuous infusion may also be used after the bolus dose.

It is also contemplated that the methods utilise a neutraceutical composition to provide the angiogenin. A nutraceutical composition for use in the methods is provided.

The term "nutraceutical" as used herein refers to an edible product isolated or purified from food, in this case from a milk product, which is demonstrated to have a physiological benefit or to provide protection or attenuation of an acute or chronic disease or injury when orally administered. The nutraceutical may thus be presented in the form of a dietary preparation or supplement, either alone or admixed with edible foods or drinks.

The nutraceutical composition may be in the form of a soluble powder, a liquid or a ready-to-drink formulation. Alternatively, the nutritional composition may be in solid form as a food; for example in the form of a ready-to-eat bar or breakfast cereal. Various flavours, fibres, sweeteners, and other additives may also be present.

The nutraceutical preferably has acceptable sensory properties (such as acceptable smell, taste and palatability), and may further comprise vitamins and/or minerals selected from at least one of vitamins A, B1, B2, B3, B5, B6, B11, B12, biotin, C, D, E, H and K and calcium, magnesium, potassium, zinc and iron.

The nutraceutical composition may be produced as is conventional; for example, the composition may be prepared by blending together the protein and other additives. If used, an emulsifier may be included in the blend. Additional vitamins and minerals may be added at this point but are usually added later to avoid thermal degradation.

If it is desired to produce a powdered nutraceutical composition, the protein may be admixed with additional components in powdered form. The powder should have a moisture content of less than about 5% by weight. Water, preferably water which has been subjected to reverse osmosis, may then be mixed in to form a liquid mixture.

If the nutraceutical composition is to be provided in a ready to consume liquid form, it may be heated in order to reduce the bacterial load. If it is desired to produce a liquid nutraceutical composition, the liquid mixture is preferably aseptically filled into suitable containers. Aseptic filling of the containers may be carried out using techniques commonly available in the art. Suitable apparatus for carrying out aseptic filling of this nature is commercially available.

Preferably the neutraceutical composition also comprises one or more pharmaceutically acceptable carriers, diluents or excipients. Neutraceutical compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives.

The nutraceutical may be an infant formula, particularly a humanised milk formula for administration to infants.

The angiogenin used in the methods of the invention may be from any source. It may be natural, synthetic or recombinant in origin. Recombinant angiogenin can be based on the angiogenin sequence from any species, including humans, cows, sheep, mouse, etc. Recombinant human angiogenin is available from R & D Systems.

Angiogenin is known to be present in normal human plasma, bovine plasma, bovine milk, bovine plasma and mouse, rabbit and pig sera. The DNA and protein sequences of at least human angiogenin are available and recombinant human angiogenin is available commercially from Abnova Corporation (Taiwan) for small scale applications.

In one embodiment the angiogenin is prepared from plasma or milk from livestock animals as readily available sources of angiogenin on a commercial scale.

The milk may be obtained from any lactating animal, e.g. ruminants such as cows, sheep, buffalos, goats, and deer, non-ruminants including primates such as a human, and monogastrics such as pigs. In a preferred embodiment the angiogenin is extracted from cow's milk. The animal from which angiogenin is produced may be a transgenic animal designed to over-express angiogenin in its milk.

The inventors of the present application have shown that in bovine milk, angiogenin is present in the highest or most concentrated amount (up to 12 mg/liter) within the first 1 to 14 days of lactation. Following this, the concentration falls to a base level of approximately 1 to 2 mg/liter. Therefore it is preferred that cow's milk which obtained within the first 14 days of lactation as a source of angiogenin for use in the methods of the first to eleventh aspects. Given the residual angiogenin levels in cow's milk from later lactation, it may still be used a source for the methods of the invention.

The angiogenin used in the methods and compositions of the invention may be isolated or purified. Purified or isolated angiogenin is substantially free of at least one agent or compound with which it is naturally associated. For instance, an isolated protein is substantially free of at least some cellular material or contaminating protein from the cell or tissue source from which it is derived. The phrase "substantially free of cellular material" refers to preparations where the angiogenin is at least 50 to 59% (w/w) pure, at least 60 to 69% (w/w) pure, at least 70 to 79% (w/w) pure, at least 80-89% (w/w) pure, at least 90-95% pure, or at least 96%, 97%, 98%, 99% or 100% (w/w) pure.

Recombinant angiogenin preparations in bacteria may be used as a source of angiogenin and may be provided in the form of protein aggregates.

As bovine milk is a natural product that has been in food chain for hundreds of years, the angiogenin used as a nutraceutical need not be totally pure. However, to reduce the amount of composition to be administered it is preferred that the angiogenin is concentrated significantly with respect to its concentration in milk. Preferably the angiogenin is administered in at a concentration of at least 10 times its concentration in milk and more preferably 20, 30, 40, or 50 times its concentration in milk.

When provided as a food the angiogenin can take the form of a food supplement, a nutritional formulation, a sports nutrition supplement or an infant formula.

Persons skilled in the art will appreciate that variants of bovine angiogenin exist in nature and can be manufactured. Use of such variants is contemplated by the present invention.

One of skill in the art will recognize that angiogenin may contain any number of conservative changes its amino acid sequence without altering its biological properties. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include arginine and lysine; glutamate and aspartate; serine and threonine; glutamine and asparagine; and valine, leucine, and isoleucine.

The present invention also includes the use of variants, homologues, and fragments of angiogenin. For example, the nucleic or amino acid sequence for angiogenin may comprise a sequence at least 70% to 79% identical to the nucleic or amino acid sequence of the native protein, or at least 80% to 89% identical, or at least 90% to 95% identical, or at least 96% to 100% identical.

Persons skilled in the art would really appreciate the numerous software packages to enable them to design or homologues of the angiogenin nucleotide and amino acid sequences, for example the "BLAST" program or other suitable packages.

It is understood by one of ordinary skill in the art that certain amino acids may be substituted for other amino acids in a protein structure without adversely affecting the activity of angiogenin. It is thus contemplated by the inventors that various changes may be made in the amino acid sequences of angiogenin without appreciable loss of their biological utility or activity. Such changes may include deletions, insertions, truncations, substitutions, fusions, shuffling of motif sequences, and the like.

In addition the angiogenin may be modified, for example by glycosylation, by conjugation to a polymer to increase their circulating half-life, by pegylation or other chemical modification. Such modified proteins are also envisaged for use in the method of the present invention.

Persons skilled in the art will appreciate that the angiogenin used may be modified to improve storage stability, bioactivity, circulating half life, or for any other purpose using methods available in the art. For example it may be desirable to introduce modification to improve storage stability. However, as angiogenin is particularly resistant to degradation such modification may not be essential.

The invention refers to agonists of angiogenin. An agonist is a compound that is capable of directly or indirectly having an effect through the receptor activated by angiogenin. Preferably angiogenin agonists act through the angiogenin receptor and preferably bind the receptor. Persons skilled in the art will appreciate how to design agonists of angiogenin. Suitable agonists include angiogenin agonist antibodies and mimetic compounds.

Angiogenin, its agonists and variants may be used in the manufacture of a medicament for use in the methods of the invention.

In a preferred embodiment of the methods and uses of the invention angiogenin is administered orally, particularly in the form of an angiogenin enriched extract from milk or plasma or in the form of recombinant angiogenin.

Particularly the orally administered angiogenin is prepared from cow's milk or a fraction thereof, for example using the process described in example 1. Such fraction has been found to provide angiogenin able to act systemically, without substantial degradation in the gut. Such fraction is able to be provided orally without employing carriers or other mechanisms to enhance the bioavailability of angiogenin.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

EXAMPLES

The invention is now further described in detail by reference to the following examples. The examples are provided for purposes of illustration only, and are not intended to be limiting unless otherwise specified. Thus, the invention encompasses any and all variations which become evident as a result of the teaching provided herein.

Example 1a

Process for the Preparation of an Angiogenin-enriched Fraction from Skim Milk

A 10 cm deep column was packed with SP Sepharose Big Beads (GE Healthcare) such that the total bed volume of the column was 29.7 liters. To the column a flow of skimmed cow's milk was applied at a linear flow rate of 331 cm/h (34 liters of skimmed milk per liter of resin per hour) for 2 hours until the volume of skimmed milk applied was 68 times the volume of the resin packed into the column.

The milk remaining in the column was removed by adding 2.5 column volumes (CV) of water at a linear flow rate of 147 cm/h (15 liters of buffer per liter of resin per hour), or 0.25 CV/min, for 10 min.

The angiogenin-depleted lactoperoxidase fraction was eluted from the column with 2.5 CV of a buffer containing sodium ions equivalent to 2.0% (0.34M) NaCl, at pH 6.5, by flowing the cation buffer solution at a linear flow rate of 75 cm/h (7.5 liters of cation buffer solution per liter of resin per hour), or 0.125 CV/min, for 20 min. The first 0.5 liters of cation buffer solution per liter of resin was discarded to drain and the next 2.5 liters of cation buffer solution per liter of resin was collected as the angiogenin-depleted lactoperoxidase fraction (including 0.5 liters of cation buffer solution per liter of resin overlapping the application time of the next buffer, i.e. breakthrough time).

The angiogenin-enriched fraction was then eluted from the column with 2.5 CV of a buffer containing sodium ions equivalent to 2.5% w/v (0.43M) NaCl, at pH 6.5, by flowing the cation buffer solution at a linear flow rate of 75 cm/h (7.5 liters of cation buffer solution per liter of resin per hour), or 0.125 CV/min, for 20 min. The first 0.5 liters of cation buffer solution per liter of resin was discarded to drain and the next 2.5 liters of cation buffer solution per liter of resin was collected as the angiogenin-enriched fraction (including 0.5 liters of cation buffer solution per liter of resin overlapping the application time of the next buffer).

Finally, the lactoferrin fraction was eluted from the column with 2.5 CV of a buffer containing sodium ions equivalent to 8.75% w/v (1.5M) NaCl, at pH 6.5, by flowing the cation buffer solution at a linear flow rate of 75 cm/h (7.5 liters of cation buffer solution per liter of resin per hour), or 0.125 CV/min, for 20 min. The first 0.5 liters of cation buffer solution per liter of resin was discarded to drain and the next 2.5 liters of cation buffer solution per liter of resin was collected as the lactoferrin fraction.

The angiogenin-enriched fraction that was collected was ultrafiltrated (NMWCO 5 kDa) to concentrate and reduce the salt content. The resultant concentrate was freeze-dried and stored at room temperature for subsequent use.

The angiogenin-enriched fraction was analysed for angiogenin content by SDS-PAGE and the fraction was found to contain 57% (protein basis) of a low molecular weight (14 kDa) protein which was confirmed to be angiogenin by MALDI-TOF/TOF MS (results not shown). The fraction was designated NatraGuard.

Persons skilled in the art would appreciate that angiogenin from other sources or purified by other means could be used in the methods of the invention.

Example 1b

Process for the Preparation of an Angiogenin-Enriched Fraction from Skim Milk

Skim milk was used to make a milk fraction containing growth factors by applying a flow of skim milk to a column packed with SP (sulphopropyl) Sepharose until the volume of milk applied was up to 120 times the volume of the resin packed into the column. The milk remaining in the column was removed with a buffer of low ionic strength (<0.008M NaCl or equivalent) for 10 min. The growth factor fraction was eluted from the column with a buffer containing sodium ions equivalent to 0.4-0.5M NaCl (though other cations would be suitable), most preferably 0.4M NaCl. A pH in the range 5.5-7.5 provides the highest yields.

A 10 cm deep column was packed with SP Sepharose Big Beads (GE Healthcare) such that the total bed volume of the column was 29.7 liters. To the column a flow of the growth factor fraction containing 1% to 1.5% protein (pH 6.5 with optional phosphate-citrate buffer) was applied at a linear flow rate of 393 cm/h (40 liters of WGFE per liter of resin per hour) for 8 min until the volume of skimmed milk applied was 5.4 times the volume of the resin packed into the column.

The angiogenin-depleted lactoperoxidase fraction was eluted from the column with 10.8 CV of a buffer containing sodium ions equivalent to 2.0% (0.34M) NaCl, at pH 6.5, by flowing the cation buffer solution at a linear flow rate of 393 cm/h (40 liters of cation buffer solution per liter of resin per hour), or 0.67 CV/min, for 16 min.

The angiogenin-enriched fraction was then eluted from the column with 5.4 CV of a buffer containing sodium ions equivalent to 2.5% w/v (0.43M) NaCl, at pH 6.5, by flowing the cation buffer solution at a linear flow rate of 393 cm/h (40 liters of cation buffer solution per liter of resin per hour), or 0.67 CV/min, for 8 min.

Finally, the lactoferrin fraction was eluted from the column with 5.4 CV of a buffer containing sodium ions equivalent to 8.75% w/v (1.5M) NaCl, at pH 6.5, by flowing the cation buffer solution at a linear flow rate of 393 cm/h (40 liters of cation buffer solution per liter of resin per hour), or 0.67 CV/min, for 8 min.

The angiogenin-enriched fraction that was collected was ultrafiltrated (NMWCO 5 kDa) to concentrate and reduce the salt content, made free of microbes by microfiltration through a 0.1 µm spiral-wound filter and finally concentrated by ultrafiltration (NMWCO 5 kDa). The resultant concentrate was freeze-dried and stored at 4-8° C. for subsequent use.

The angiogenin-enriched fraction was analysed for angiogenin content by cation exchange HPLC and the fraction was found to contain 39.4% (protein basis) of a low molecular weight (14 kDa) protein which was confirmed to be angiogenin by MALDI-TOF/TOF MS (results not shown). The fraction was designated NatraGuard.

Persons skilled in the art would appreciate that angiogenin from other sources or purified by other means could be used in the methods of the invention.

Example 2

Angiogenin was provided in an enriched extract prepared from bovine skim-milk according to the method described in Example 1b.

Eight week old female BALB/c nu/nu nude mice (Animal Resource Centre, Western Australia) were acclimatized for one week prior to injection of cancer cell lines. Standard chow and water was provided ad libitum. Food and water was weighed throughout the experimental period to ensure weight loss in the cancer control group was not due to a decrease in caloric intake. Animals were randomised to three weight matched groups consisting of cancer no treatment (control), cancer supplemented with a diet containing NatraGuard 60 µg/g of food (60 µg NatraGuard) and cancer supplemented with a diet containing NatraGuard 300 µg/g of food (300 µg NatraGuard).

The murine adeno-carcinoma (MAC) cell line 16 (MAC16) which produces a tumour was cultured in RPMI with 10% FBS and 0.5% penicillin/streptomycin (Invitrogen). Cells were kept in a humidified incubator at 37° C. in 10% $CO_2$. Cells were grown to 80% confluence and removed from cell culture flasks via trypsinization. These cells were centrifuged at 500 xg for 5 minutes at 4° C. and isolated from the growth media. Cells were then resuspended in sterile PBS pre-incubated to 37° C. and drawn up into a sterile syringe with a 25 gauge needle for subsequent injection into mice. Mouse tumour volumes were measured using callipers. Animals were euthanased before weight loss in the control group reached 25% of their initial weight or before tumour growth exceeded 1000 $mm^3$. Tissues were harvested and immediately placed in liquid nitrogen before storing in a −80° C. freezer for analysis.

The current investigation is the first study to feed NatraGuard to mice with some form of cancer. Thus it was important to ensure that supplementation with NatraGuard did not enhance tumour growth or cause other negative health outcomes in the mice.

Figure 1:
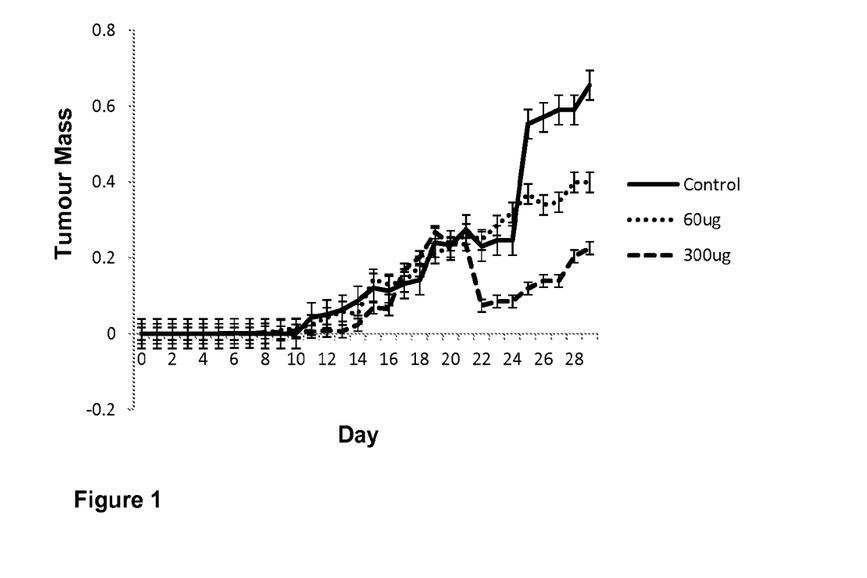
FIG. 1 shows the effect of supplementation with an angiogenin enriched milk fraction on mean tumour growth in nude mice after induction of cancer. Decreases in tumour size after day 15 are due to animals being euthanized and the mean value changing due to reduced group size (a result of ethical guidelines that instruct that animals must be euthanized when body weight reaches 25% of baseline weight or when tumour volume reaches 1000 mm 3; whichever occurs first).

Supplementation with NatraGuard had no effect on the induction of cancer in the mouse model (Table 1). Visible or palpable tumours were detected at the site of MAC16 cell injection by day 12.2±1.0 in control mice, day 13.3±1.6 in mice supplemented with 60 ug NatraGuard and day 14.3±2.6 in mice supplemented with 300 ug NatraGuard. Similarly supplementation with NatraGuard had no effect on the growth rate of tumours (FIG. 1). The final mean tumour size was not different between any of the groups (Table 1), 313±187 mm³ (cachexia), 412±88 mm³ (60 ug NatraGuard) and 334±114 mm³ (300 ug NatraGuard). There were no metastases present in any group.

TABLE 1

The effect of NatraGuard supplementation

|  | Cachexia | 60 ug NG | 300 ug NG |
|---|---|---|---|
| Tumour 1$^{st}$ present (day) | 12.2 ± 1.0 | 13.3 ± 1.6 | 14.3 ± 2.6 |
| Final tumour size (mm³) | 313 ± 187 | 412 ± 88 | 334 ± 114 |

Figure 2:
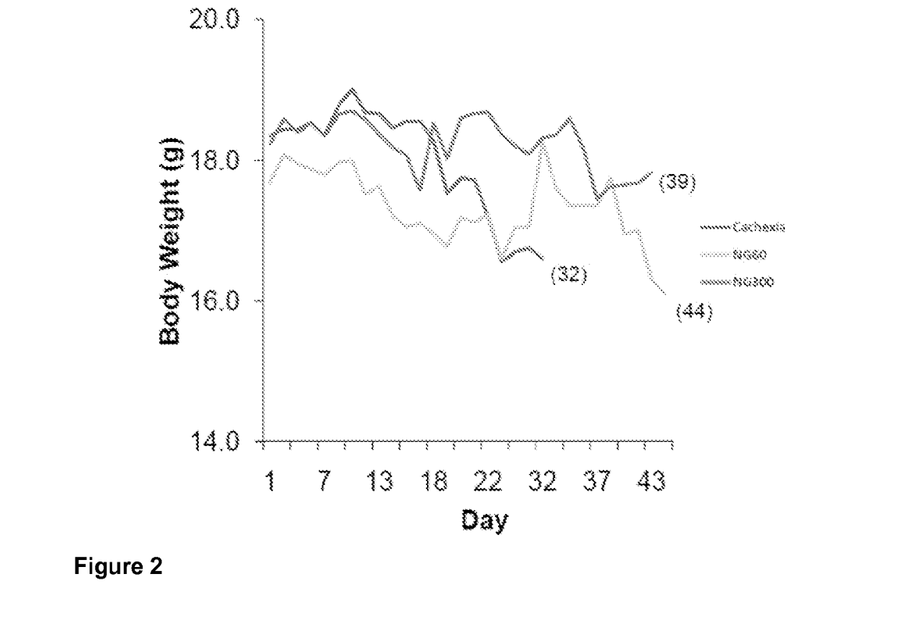
FIG. 2 shows the survival rate of animals tested in accordance with Example 2.

Results suggest that NatraGuard, the bovine milk extract enriched for angiogenin, made by the method described in Example 1b, is capable of prolonging life (survival rate—see FIG. 2), and delaying presence of the tumour at both doses compared to control.

Example 3

Figure 3:
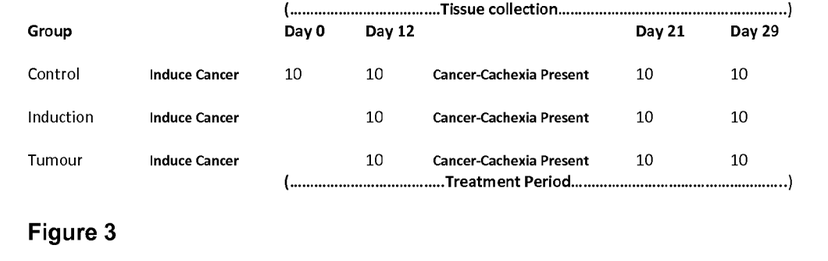
FIG. 3 shows the study design for Example 3.

Mice were injected with the murine adenocarcinoma 16 (MAC16) cell line, then randomized into 3 groups, consisting of cancer cachexia (Control), cancer cachexia supplemented with a diet containing NatraGuard 300 ug/g of food, with supplementation to start at the time of cancer induction (Induction) and cancer cachexia supplemented with a diet containing NatraGuard 300 ug/g of food, with supplementation to start at the time when a tumour is first detectable (Tumour). Animals were monitored daily for changes in body weight, tumour size measured using callipers, food intake and water intake. Groups of 10 mice from each treatment were terminated by sodium pentobarbital injection (30 mg/kg) at day 0, 12, 21 and 29 post cancer induction or when weight loss reached 25%, or tumour size reached 1000 mm³, whichever occurred first. Muscle tissues, including gastrocnemius and quadriceps along with the heart were removed and weighed. All samples were snap frozen and stored at −80° C. The study design is summarized in FIG. 3.

Effect of NatraGuard on Cancer Induction

Supplementation with NatraGuard from the time of cancer Induction significantly delayed the onset of when a tumour could first be detected by two days compared to the Control and Tumour groups (Table 2, P<0.005). The final mean tumour size was not different between any of the groups (Table 2). There were no metastases present in any group.

TABLE 2

Tumour characteristics.

|  | Control | Induction | Tumour |
|---|---|---|---|
| Tumour 1$^{st}$ present (day) | 12.3 ± 0.2 | 14.9 ± 0.4* | 13.0 ± 0.3 |
| Final tumour size (mm³) | 655 ± 211 | 226 ± 97 | 399 ± 145 |

*Significantly different from Control and Tumour groups P < 0.005.

Supplementation with NatraGuard at the dose of 300 ug/g of food from the time of cancer induction delayed the onset of tumour development and reduced the final tumour size.

The invention claimed is:

1. A method of preventing or delaying tumor onset in a subject, said subject being susceptible to developing a malignancy, a cancer, or any neoplastic disease or disorder, as identified by the subject being positive for one or more cancer markers, the method comprising administering to the subject an effective amount of angiogenin.

2. The method of claim 1 in which angiogenin is provided as a milk extract enriched for angiogenin, optionally by cation exchange.

3. The method of claim 1 in which the angiogenin is administered orally.

4. The method of claim 1 in which the angiogenin is administered in a nutraceutical.

5. The method of claim 4 in which the nutraceutical is a dietary supplement.

6. The method of claim 1 in which the effective amount of angiogenin is equivalent to a dose of 60 to 300 microgram per gram of food for a mouse.

7. A method of preventing or delaying tumor onset in a subject having a stage I or stage II cancer, the method comprising administering to the subject an effective amount of angiogenin.

* * * * *